United States Patent

Kumagai et al.

[11] Patent Number: 5,998,631
[45] Date of Patent: Dec. 7, 1999

[54] CYCLIC PHENOL SULFIDE HAVING AT LEAST ONE SULFINYL OR SULFONYL GROUP AND PROCESS FOR PRODUCING THE SAME

[75] Inventors: Hitoshi Kumagai; Setsuko Miyanari, both of Saitama; Sotaro Miyano, Miyagi, all of Japan

[73] Assignees: Cosmo Research Institute; Cosmo Oil Co., Ltd., both of Tokyo, Japan

[21] Appl. No.: 09/068,583

[22] PCT Filed: Aug. 8, 1997

[86] PCT No.: PCT/JP97/02789

§ 371 Date: May 6, 1998

§ 102(e) Date: May 6, 1998

[87] PCT Pub. No.: WO98/09959

PCT Pub. Date: Mar. 12, 1998

[30] Foreign Application Priority Data

Sep. 6, 1996 [JP] Japan .................................. 8-255368

[51] Int. Cl.[6] .................................................. C07D 409/14
[52] U.S. Cl. .................................................................. 549/11
[58] Field of Search ........................................ 549/1, 2, 11

[56] References Cited

FOREIGN PATENT DOCUMENTS 0 731 102   9/1996   European Pat. Off. ...... C07D 341/00

OTHER PUBLICATIONS

Z. Aryan et al.: "Action of Sulfur Monochloride on Aromatic Ethers" Journal of the Chemical Society., 1962, pp. 4709–4712, XP000568857 Letchworth GB.

Kumagai, Hitoshi et al., "Facule Synthesis of p–tert–Butylthiacalix(4)arene by the Reaction of p–tert–Butylphenol with Elemental Sulfur in the Presence of a Base." Tetrahedron Letters, vol. 38, No. 22, Elserver Science Ltd. (England) (1997) pp. 3971–3972.

Sone, Tyo. et al., "Synthesis and Properties of Sulfur–Bridged Analog of p–tert–Butylthiacalix(4)arene." Tetrahedron, vol. 38, No. 22, Elserver Science Ltd. (England) (1997) pp. 10689–10698.

*Primary Examiner*—Robert W. Ramsuer
*Assistant Examiner*—Ebenezer Sackey
*Attorney, Agent, or Firm*—Sughrue, Mion, Zinn, Macpeak & Seas, PLLC

[57] ABSTRACT

A cyclic phenol sulfide containing at least one sulfinyl or sulfonyl group represented by formula (1):

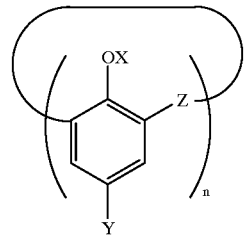

(1)

wherein X represents a hydrogen atom, a hydrocarbon group, or an acyl group; Y represents a hydrogen atom, a hydrocarbon group, a halogenated hydrocarbon group, —$COR^1$, —$OR^2$, —$COOR^3$, —CN, —$CONH_2$, —$NO_2$, —$NR^4R^5$, a halogen atom, —$SO_4R^6$, or —$SO_3R^7$, in which $R^1$, $R^2$, $R^3$, $R^4$, $R^5$, $R^6$, and $R^7$ each represents a hydrogen atom or a hydrocarbon group; Z represents one member selected from the group consisting of S, a sulfinyl group, and a sulfonyl group; and n represents an integer of 4 to 12, provided that the plural X's or the plural Y's are the same or different, and that at least one of the plural Z's is a sulfinyl group or a sulfonyl group, and a process for producing the same.

6 Claims, No Drawings

CYCLIC PHENOL SULFIDE HAVING AT LEAST ONE SULFINYL OR SULFONYL GROUP AND PROCESS FOR PRODUCING THE SAME

This application is a 371 of PCT/JP97/02789 filed on Aug. 8, 1997.

TECHNICAL FIELD

The present invention relates to a novel cyclic phenol sulfide having at least one sulfinyl or sulfonyl group which can be used as, e.g., a metal-trapping agent, an ion sensor, a sensor with substrate specificity, a separating-membrane material, a polymer material, an oxidizing catalyst, a phase-transfer catalyst, a synthetic enzyme, a light energy converter, or an intermediate for functional molecules using a recognition ability of an ion or molecule, and a process for producing the same.

BACKGROUND ART

Alkylphenol sulfides are conventionally known as an antioxidant (e.g., U.S. Pat. Nos. 2,239,534, 3,377,334), a rubber sulfurizer (e.g., U.S. Pat. Nos. 3,468,961, 3,647,885), a polymer stabilizer (e.g., U.S. Pat. Nos. 3,882,082, 3,845, 013, 3,843,600), an anticorrosive (e.g., U.S. Pat. No. 3,684, 587), and a starting material for phenates for use as a lubricating-oil additive (Hori et al., Sekiyu Gakkai-shi, Vol. 34, p. 446, 1991).

Known processes for producing conventional phenol sulfides include a method in which a phenol and elemental sulfur are used as starting materials (e.g., A. J. Neale et al., *Tetrahedron*, Vol. 25, p. 4593, 1969); a method in which a phenol, elemental sulfur, and a base catalyst are used as starting materials (e.g., U.S. Pat. No. 3,468,961); a method in which a phenol, elemental sulfur, and a molecular halogen are used as starting materials (e.g., B. Hortling et al., *Polym. Bull.*, Vol. 8 (1982), p.1); a method in which a phenol reacts with an aryl disulfide in the presence of a base catalyst (e.g., T. Fujisawa et al., *J. Org. Chem.*, Vol. 33 (1973), p.687); a method in which a phenol and a sulfur halide are used as starting materials (e.g., U.S. Pat. No. 2,239,534); and a method in which a halogenated phenol reacts with a sulfurized alkali metal reagent.

However, they disclose an oligomer containing 2,2'-thiobis(4-alkylphenol) (dimer), 2-[3-(2-hydroxy-5-alkylphenylthio)-2-hydroxy-5-alkylphenylthio]-4-alkylphenol (trimer), or 2-[3-[3-(2-hydroxy-5-alkylphenylthio)-2-hydroxy-5-alkylphenylthio]-2-hydroxy-5-alkylphenylthio]-4-alkylphenol (tetramer), or a composition containing such an oligomer, and a process for the production thereof. Namely, the alkylphenol sulfides dealt with in those references are all non-cyclic compounds, and the existence of a cyclic phenol sulfide and a method for producing the same have not been disclosed.

DISCLOSURE OF THE INVENTION

An object of the present invention is to provide a novel cyclic phenol sulfide having at least one sulfinyl or sulfonyl group and a process for producing the same.

The present inventors made intensive studies in order to accomplish the above object. As a result, they have found the existence of a novel cyclic phenol sulfide having at least one sulfinyl or sulfonyl group and that it is obtained from a cyclic phenol sulfide represented by formula (2):

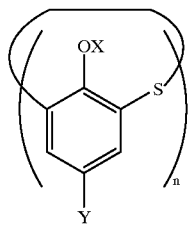

wherein X represents a hydrogen atom, a hydrocarbon group, or an acyl group; Y represents a hydrogen atom, a hydrocarbon group, a halogenated hydrocarbon group, $-COR^1$, $-OR^2$, $-COOR^3$, $-CN$, $-CONH_2$, $-NO_2$, $-NR^4R^5$, a halogen atom, $-SO_4R^6$, or $-SO_3R^7$, in which $R^1$, $R^2$, $R^3$, $R^4$, $R^5$, $R^6$, and $R^7$ each represents a hydrogen atom or a hydrocarbon group; and n represents an integer of 4 to 12, provided that the plural X's or the plural Y's are the same or different, by oxidizing a sulfide bond in the compound. They have further found a process for producing the compound. The present invention has been completed based on these findings.

Accordingly, the present invention provides a cyclic phenol sulfide having at least one sulfinyl or sulfonyl group represented by formula (1):

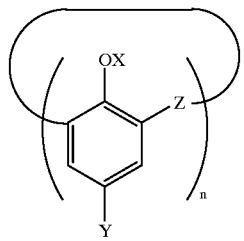

wherein X represents a hydrogen atom, a hydrocarbon group, or an acyl group; Y represents a hydrogen atom, a hydrocarbon group, a halogenated hydrocarbon group, $-COR^1$, $-OR^2$, $-COOR^3$, $-CN$, $-CONH_2$, $-NO_2$, $-NR^4R^5$, a halogen atom, $-SO_4R^6$, or $-SO_3R^7$, in which $R^1$, $R^2$, $R^3$, $R^4$, $R^5$, $R^6$, and $R^7$ each represents a hydrogen atom or a hydrocarbon group; Z represents one member selected from the group consisting of S, a sulfinyl group, and a sulfonyl group; and n represents an integer of 4 to 12, provided that the plural X's or the plural Y's are the same or different, and that at least one of the plural Z's is a sulfinyl group or a sulfonyl group. The present invention further provides a process for producing the same.

The present invention will be explained below in detail.

In formula (1), X represents a hydrogen atom, a hydrocarbon group, or an acyl group.

The carbon atom number of the hydrocarbon group represented by X is not particularly limited as long as the number is 1 or more. Preferably, the carbon atom number of the hydrocarbon group is from 1 to 50. Examples of the hydrocarbon group include a saturated aliphatic hydrocarbon group, an unsaturated aliphatic hydrocarbon group, an alicyclic hydrocarbon group, an alicyclic-aliphatic hydrocarbon group, an aromatic hydrocarbon group, and an aromatic-aliphatic hydrocarbon group.

Preferred examples of the saturated aliphatic hydrocarbon group include an alkyl group such as methyl, ethyl, n-propyl, isopropyl, n-butyl, isobutyl, tert-butyl, n-pentyl, isopentyl, neopentyl, tert-pentyl, 2-methylbutyl, n-hexyl, isohexyl, 3-methylpentyl, ethylbutyl, n-heptyl, 2-methylhexyl, n-octyl, isooctyl, tert-octyl, 2-ethylhexyl, 3-methylheptyl, n-nonyl, isononyl, 1-methyloctyl, ethylheptyl, n-decyl, 1-methylnonyl, n-undecyl, 1,1-dimethylnonyl, n-dodecyl, n-tetradecyl, n-heptadecyl, and n-octadecyl groups; and a hydrocarbon group derived from a polymer or copolymer of ethylene, propylene, or butylene.

Preferred examples of the unsaturated aliphatic hydrocarbon group include alkenyl and alkynyl groups such as vinyl, allyl, isopropenyl, 2-butenyl, 2-methylallyl, 1,1-dimethylallyl, 3-methyl-2-butenyl, 3-methyl-3-butenyl, 4-pentenyl, hexenyl, octenyl, nonenyl, and decenyl groups; and a hydrocarbon group derived from a polymer or copolymer of acetylene, butadiene, or isoprene.

Preferred examples of the alicyclic hydrocarbon group include cycloalkyl, cycloalkenyl, and cycloalkynyl groups such as cyclopropyl, cyclobutyl, cyclopentyl, cyclohexyl, cycloheptyl, cyclooctyl, 3-methylcyclohexyl, 4-methylcyclohexyl, 4-ethylcyclohexyl, 2-methylcyclooctyl, cyclopropenyl, cyclobutenyl, cyclopentenyl, cyclohexenyl, cycloheptenyl, cyclooctenyl, 4-methylcyclohexenyl, and 4-ethylcyclohexenyl groups.

Preferred examples of the alicyclic-aliphatic hydrocarbon group include cycloalkyl-, cycloalkenyl-, or cycloalkynyl-substituted alkyl, alkenyl, and alkynyl groups such as cyclopropylethyl, cyclobutylethyl, cyclopentylethyl, cyclohexylmethyl, cyclohexylethyl, cycloheptylmethyl, cyclooctylethyl, 3-methylcyclohexylpropyl, 4-methylcyclohexylethyl, 4-ethylcyclohexylethyl, 2-methylcyclooctylethyl, cyclopropenylbutyl, cyclobutenylethyl, cyclopentenylethyl, cyclohexenylmethyl, cycloheptenylmethyl, cyclooctenylethyl, 4-methylcyclohexenylpropyl, and 4-ethylcyclohexenylpentyl groups.

Preferred examples of the aromatic hydrocarbon group include an aryl group such as phenyl and naphthyl groups; and alkylaryl, alkenylaryl, and alkynylaryl groups such as 4-methylphenyl, 3,4-dimethylphenyl, 3,4,5-trimethylphenyl, 2-ethylphenyl, n-butylphenyl, tert-butylphenyl, amylphenyl, hexylphenyl, nonylphenyl, 2-tert-butyl-5-methylphenyl, cyclohexylphenyl, cresyl, oxyethylcresyl, 2-methoxy-4-tert-butylphenyl, and dodecylphenyl. The alkyl moiety of the alkylaryl group, the alkenyl moiety of the alkenylaryl group, and the alkynyl moiety of the alkynylaryl group may have a cyclic structure.

Preferred examples of the aromatic-aliphatic hydrocarbon group include aralkyl, aralkenyl, and aralkynyl groups such as benzyl, 1-phenylethyl, 2-phenylethyl, 2-phenylpropyl, 3-phenylpropyl, 4-phenylbutyl, 5-phenylpentyl, 6-phenylhexyl, 1-(4-methylphenyl)ethyl, 2-(4-methylphenyl)ethyl, 2-methylbenzyl, and 1,1-dimethyl-2-phenylethyl groups. The alkyl moiety of the aralkyl group, the alkenyl moiety of the aralkenyl group, and the alkynyl moiety of the aralkynyl group may have a cyclic structure.

The carbon atom number of the acyl group is not particularly limited as long as the number is 1 or more.

Preferably, the carbon atom number of the acyl group is from 1 to 40. Preferred examples of the acyl group include formyl, acetyl, propionyl, butyryl, isobutyryl, valeryl, isovaleryl, oxalyl, succinyl, pivaloyl, stearoyl, benzoyl, phenylpropionyl, toluoyl, naphthoyl, phthaloyl, indancarbonyl, p-methylbenzoyl, and cyclohexylcarbonyl groups.

In formula (1), Y represents a hydrogen atom, a hydrocarbon group, a halogenated hydrocarbon group, —$COR^1$, —OR , —$COOR^3$, —CN, —$CONH_2$, —$NO_2$, —$NR^4R^5$, a halogen atom, —$SO_4R^6$, or —$SO_3R^7$.

Examples of the hydrocarbon group and the —$COR^1$ group both represented by Y include the same hydrocarbon groups and acyl groups as those enumerated hereinabove with regard to X. Preferred examples thereof also include the same preferred groups.

Examples of the halogenated hydrocarbon group include halogenated hydrocarbon groups formed by halogen-substituting the same hydrocarbon groups as those enumerated hereinabove with regard to X. Preferred examples thereof also include halogenated hydrocarbon groups derived from the same preferred hydrocarbon groups.

$R^1$, $R^2$, $R^3$, $R^4$, $R^5$, $R^6$, and $R^7$ each represents a hydrogen atom or a hydrocarbon group. Examples of the hydrocarbon group include the same hydrocarbon groups as those enumerated hereinabove with regard to X, and preferred examples thereof also include the same preferred groups.

The above hydrocarbon group may be substituted with at least one substituent such as —$COR^1$, —$OR^2$, —$COOR^3$, —CN, —$CONH_2$, —$NO_2$, —$NR^4R^5$, a halogen atom, —$SO_4R^6$, or —$SO_3R^7$.

The halogen atom may be any of fluorine, chlorine, bromine, and iodine atoms.

These substituents may be of one kind or two or more kinds. The number of the substituents may be one or more per hydrocarbon group.

In formula (1), the number of X's present is from 4 to 12 per molecule. The plural X's are the same or different.

In formula (1), the number of Y's present is from 4 to 12 per molecule. The plural Y's are the same or different.

Furthermore, in formula (1), the number of Z's present is from 4 to 12 per molecule, and at least one of the plural Z's is a sulfinyl group or a sulfonyl group.

A process for producing the cyclic phenol sulfide of the present invention containing at least one sulfinyl or sulfonyl group will be explained next.

The cyclic phenol sulfide containing at least one sulfinyl or sulfonyl group according to the present invention can be produced by oxidizing a sulfide bond in a cyclic phenol sulfide represented by formula (2), wherein X represents a hydrogen atom, a hydrocarbon group, or an acyl group; Y represents a hydrogen atom, a hydrocarbon group, a halogenated hydrocarbon group, —$COR^1$, —$OR^2$, —$COOR^3$, —CN, —$CONH_2$, —$NO_2$, —$NR^4R^5$, a halogen atom, —$SO_4R^6$, or —$SO_3R^7$, in which $R^1$, $R^2$, $R^3$, $R^4$, $R^5$, $R^6$, and $R^7$ each represents a hydrogen atom or a hydrocarbon group; and n represents an integer of 4 to 12, provided that the plural X's or the plural Y's are the same or different.

In formula (2), X represents a hydrogen atom, a hydrocarbon group, or an acyl group, and examples thereof are the same as those for the X in formula (1) described above.

In formula (2), Y represents a hydrogen atom, a hydrocarbon group, a halogenated hydrocarbon group, —$COR^1$, —$OR^2$, —$COOR^3$, —CN, —$CONH_2$, —$NO_2$, —$NR^4R^5$, a halogen atom, —$SO_4R^6$, or —$SO_3R^7$, wherein $R^1$, $R^2$, $R^3$, $R^4$, $R^5$, $R^6$, and $R^7$ each represents a hydrogen atom or a hydrocarbon group. Examples thereof are the same as those for the Y in formula (1) described above.

In formula (2), the number of X's present is from 4 to 12 per molecule. The plural X's are the same or different.

In formula (2), the number of Y's present is from 4 to 12 per molecule. The plural Y's are the same or different.

A preferred process for producing a cyclic phenol sulfide represented by formula (2) comprises first reacting a phenol compound represented by formula (3):

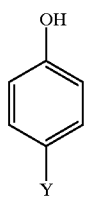

(3)

wherein Y represents a hydrogen atom or a hydrocarbon group, which is unsubstituted phenol or has a hydrocarbon group in the 4-position of the benzene ring to the hydroxyl group, with an appropriate amount of elemental sulfur in the presence of an appropriate amount of at least one metallic reagent selected from alkali metal reagents and alkaline earth metal reagents.

The phenol compound and elemental sulfur used as starting materials are fed in such a proportion that the amount of the elemental sulfur is at least 0.1 gram equivalent, preferably at least 0.35 gram equivalents, per gram equivalent of the phenol compound. Although there is no particular upper limit on the proportion of the elemental sulfur fed as a raw material, the amount thereof is preferably up to 20 gram equivalents, especially preferably up to 10 gram equivalents, per gram equivalent of the phenol compound.

Examples of the alkali metal reagents include elemental alkali metals, alkali metal hydrides, alkali metal hydroxides, alkali metal carbonates, alkali metal alkoxides, and alkali metal halides. Examples of the alkaline earth metal reagents include elemental alkaline earth metals, alkaline earth metal hydrides, alkaline earth metal hydroxides, alkaline earth metal oxides, alkaline earth metal carbonates, alkaline earth metal alkoxides, and alkaline earth metal halides.

The use amount of the alkali metal reagent or alkaline earth metal reagent is at least 0.005 gram equivalents, preferably at least 0.01 gram equivalent, per gram equivalent of the phenol compound. Although there is no particular upper limit on the use amount of the alkali metal reagent or alkaline earth metal reagent, the amount thereof is preferably less than 10 gram equivalents, especially preferably less than 5 gram equivalents.

The hydrogen atom of the hydroxyl group can be suitably converted, if desired, to a hydrocarbon group or acyl group by etherification, acylation, or the like. If Y is a hydrogen atom, the hydrogen atom is directly replaced with a substituent. If Y is an alkyl group, a dealkylation reaction is conducted, followed by conversion of the substituent. Thus, a cyclic phenol sulfide represented by formula (2) can be produced.

Methods for the replacement of a substituent include a method in which a cyclic phenol sulfide represented by formula (2) described above in which Y is an alkyl group is dealkylated with an aluminum chloride or cobalt oxide catalyst or the like to convert each alkyl group to hydrogen. or cobalt oxide catalyst or the like to convert each alkyl group to hydrogen.

Another method for replacement of a substituent comprises causing an appropriate nitrating agent, e.g., nitronium tetrafluoroborate or nitric acid, to act on the dealkylated cyclic phenol sulfide to convert the hydrogen atoms introduced by the dealkylation to nitro groups.

The nitro groups can be converted to amino groups by reduction with an appropriate reducing agent, e.g., iron/hydrochloric acid. Furthermore, it is also possible to diazotize the resultant compound with sodium nitrate or the like and cause an appropriate halogenating agent, e.g., copper chloride, a cyano-introducing agent, or water to act on the diazotization product in the presence of hydrochloric acid or the like to convert the diazo groups to halogen atoms, cyano groups, or hydroxyl groups, respectively.

The hydroxyl groups can be converted to acid sulfuric ester groups by the reaction of a sulfuric ester-forming agent, e.g., sulfuric acid.

The hydroxyl groups can also be converted to alkyl ether groups by forming an alkali metal phenoxide, e.g., sodium phenoxide, and causing an alkyl halide to act thereon. hydrogen atoms introduced by the dealkylation can be converted to sulfo groups.

Also, there is a method in which the dealkylated cyclic phenol sulfide is allowed to react with an acid halide, if desired in the presence of a Lewis acid or the like, whereby the hydrogen atoms introduced by the dehydration can be converted to acyl groups.

The cyclic phenol sulfide represented by formula (2) thus synthesized can be converted to a cyclic phenol sulfide containing at least one sulfinyl or sulfonyl group by oxidizing the sulfide bond thereof.

A general oxidizing agent can be used to conduct the oxidation reaction of sulfide bonds. Appropriate oxidizing agents include hydrogen peroxide, organic peroxides, peracids, halogen oxides, N-halogenated imido compounds, molecular halogens, oxygen, ozone, nitric acid, inorganic oxides, and the like. Preferred oxidizing agents include hydrogen peroxide, molecular halogens, and inorganic oxides.

Preferred examples of the organic peroxides include t-butyl peracetate, perbenzoic acid, m-chloroperbenzoic acid, and benzoyl peroxide.

Preferred examples of the peracids include peracetic acid, trifluoroperacetic acid, and bis(trimethylsilyl) peroxide.

Preferred examples of the halogen oxides include sodium periodate, sodium hypochlorite, sodium bromite, and iodobenzenes.

Preferred examples of the N-halogenated imido compounds include N-bromosuccinimide and N-chlorosuccinimide.

Examples of the molecular halogens include chlorine, bromine, and iodine. Especially preferred is bromine.

Preferred examples of the inorganic oxides include manganese (IV) oxide, cerium (IV) oxide, ruthenium (IV) oxide, chromium (IV) oxide, lead (IV) tetraacetate, sodium perborate, and permanganic acid salts. Especially preferred is sodium perborate.

These oxidizing agents may be used alone or in combination of two or more thereof.

With respect to the incorporation amount of the oxidizing agent used, the oxidation number for sulfur can be changed by changing the amount by equivalent of the oxidizing agent added based on the amount of the sulfide bonds of the cyclic phenol sulfide represented by formula (2). In general, sulfinyl bonds are apt to generate when the oxidizing agent is added in an amount nearly equivalent to the sulfide bonds, usually from 1.0 to 1.5 gram equivalents, preferably from 1.0 to 1.2 gram equivalents, per gram equivalent of the sulfide bonds. On the other hand, sulfonyl bonds are apt to generate when the oxidizing agent is used in excess, usually in an amount of from 2 to 10 gram equivalents, preferably from 2 to 6 gram equivalents, per gram equivalent of the sulfide bonds.

A catalyst may be used for the reaction if necessary.

Preferred examples of the catalyst of using, for example, hydrogen peroxide as an oxidizing agent include vanadium (V) oxide, sodium metavanadate (V), titanium trichloride, tungsten (VI) oxide, and sodium phosphate. These catalysts may be used alone or in combination of two or more thereof.

Although the use amount of the catalyst is not particularly limited, it is generally from 0.005 to 10 gram equivalents, preferably from 0.01 to 6 gram equivalents, per gram equivalent of the sulfide bond.

The oxidation reaction can also be conducted using electrochemical and photochemical techniques. Furthermore, an enzyme can be used to conduct the oxidation.

Examples of the solvent to be used include chlorinated solvents such as chloroform and dichloromethane, alcohols such as methanol and ethanol, and protonic solvents such as acetonitrile, acetic acid, and water. Although any desired solvent can be used as long as it does not inhibit the intended reaction, preferred solvents vary depending on the oxidation conditions used, generally as follows. An alcohol solvent, e.g., methanol, ethanol, or butanol, or a chlorinated solvent, e.g., chloroform or dichloromethane, is preferred if hydrogen peroxide or an organic oxide is used as an oxidizing agent; a solvent such as water, acetonitrile, or trifluoroacetic acid is preferred if a peracid is used as an oxidizing agent; a solvent such as methanol/water, acetone, or dioxane is preferred if a halogen oxide is used as an oxidizing agent; an alcohol solvent, e.g., methanol, is preferred if an N-halogenated compound is used as an oxidizing agent; and a two-phase system consisting of a chlorinated solvent, e.g., chloroform or dichloromethane, and a weakly alkaline aqueous solution, e.g., an aqueous solution of a hydrogen carbonate, is preferred if a molecular halogen is used as an oxidizing agent. Furthermore, a solvent such as water or cyclohexane is preferred nitric acid is used as an oxidizing agent; on the other hand, dichloromethane is preferred if ozone for the oxidation is used. If an inorganic oxide is used, it is preferred to use pyridine, acetonitrile, acetic acid, a hydrocarbon, a chlorinated solvent, e.g., dichloromethane or chloroform, or a solvent consisting of a mixture thereof. In the case where an electrochemical technique is used to conduct the oxidation, a solvent such as acetonitrile or acetic acid is preferably used. In the case where a photochemical technique is used to conduct the oxidation, a chlorinated solvent, e.g., chloroform or dichloromethane, or methanol is preferably used. These solvents may be used alone or in combination of two or more thereof.

Although the use amount of the solvent is not particularly limited, it may be generally from 5 to 100 ml, preferably from 10 to 50 ml, per g of the cyclic phenol sulfide.

Reaction temperatures are preferably from −78° C. to 100° C. However, the preferred temperatures vary depending on the oxidizing agents used. Specifically, temperatures of from 15° C. to 65° C. are preferred if hydrogen peroxide, oxygen, nitric acid, or an inorganic oxide is used as an oxidizing agent; temperatures of from −10° C. to 90° C. are preferred if an organic peroxide or a peracid is used as an oxidizing agent; and temperatures of from −10° C. to 30° C. are preferred if a molecular halogen or a halogen oxide is used. Furthermore, if ozone for the oxidation is used, the reaction is preferably conducted at −78° C. In the case where an electrochemical technique or a photochemical technique is used for the oxidation, the reaction is preferably conducted at a temperature of from 20° C. to 60° C.

The period of this reaction is not particularly limited, and an appropriate reaction period may be used according to the kind and incorporation amount of the oxidizing agent. In general, a reaction period of from 0.5 to 120 hours may be used.

In the case where a reaction product comprising a mixture of oxidative derivatives differing in oxidation number was obtained, these derivatives may be separated by an ordinary separation technique, e.g., recrystallization.

BEST MODES FOR CARRYING OUT THE INVENTION

The present invention will be explained below in more detail by reference to Production Example, Examples, and Application Example, the invention should not be construed as being limited thereby in any way.

PRODUCTION EXAMPLE

Synthesis of 5,11,17,23-tetra-tert-butyl-25,26,27,28-tetrahydroxy-2,8,14,20-tetrathia-[19.3.1.1$^{3,7}$1$^{9,13}$1$^{15,19}$]octacosa-1(25), 3,5,7(28),9,11,13(27),15,17,19(26),21,23-dodecaene (I)

To 45.2 g of 4-tert-butylphenol were added 14.4 g of elemental sulfur and 3.0 g of sodium hydroxide. The mixture was gradually heated to 230° C. over a period of 4 hours with stirring in a nitrogen atmosphere, and then stirred for further 2 hours. During the stirring, the water and hydrogen sulfide which were generated by the reaction were removed. The water recovered by distillation during the reaction amounted to about 0.8 g, while the hydrogen sulfide generated by the reaction amounted to about 6 g. The resultant reaction mixture was cooled to room temperature, and 500 ml of ether was added thereto to dissolve the same. Thereafter, the reaction mixture was hydrolyzed with 1N aqueous sulfuric acid solution. The ether layer obtained through liquid separation was washed with water and dried over magnesium sulfate. The ether was distilled off, and the reaction mixture thus obtained was separated by silica gel column chromatography (hexane/chloroform) to obtain a crude reaction product, which was recrystallized from chloroform/acetone. Thus, 4.32 g of a reaction product (I) was obtained as colorless crystals.

This reaction product (I) is the cyclic alkylphenol sulfide represented by formula (2) wherein X=H, Y=t-Bu (tert-butyl), and n=4.

Properties of this reaction product (I) are shown below.

Melting point: 320–322° C.

$^1$H-NMR: (δ, ppm, CDCl$_3$) 9.60 (s, 4H, OH), 7.64 (s, 8E, ArH), 1.22 (s, 36H, C(CH$_3$)$_3$)

$^{13}$C-NMR: (δ, ppm, CDCl$_3$) 155.6, 144.7, 136.4, 120.5 (Ar), 34.2 (C(CH$_3$)$_3$), 31.3 (C(CH$_3$)$_3$)

IR: (cm$^{-1}$, KRS-5): 3324 (OH), 2962 (CH)

MS m/z: 720 (M$^+$)

Elemental analysis %:

Calculated for C$_{40}$H$_{48}$O$_4$S$_4$: C, 66.62; H, 6.71; S, 17.79,

Found: C, 66.37; H, 6.57; S, 17.22

EXAMPLE 1

Synthesis of 5,11,17,23-tetra-tert-butyl-25,26,27,28-tetrahydroxy-2,8,14,20-tetrasulfinyl-[19.3.1.1$^{3,7}$1$^{9,13}$1$^{15,19}$]octacosa-1(25),3,5,7(28),9,11,13(27),15,17,19(26),21,23-dodecaene (II)

In 30 ml of chloroform was dissolved 1.8 g of 5,11,17,23-tetra-tert-butyl-25,26,27,28-tetrahydroxy-2,8,14,20-tetrathia[19.3.1.1$^{3,7}$1$^{9,13}$1$^{15,19}$]-octacosa-1(25),3,5,7(28),9,11,13(27),15,17,19(26),21,23-dodecaene (I), represented by formula (2) wherein X=H, Y=t-Bu, and n=4. A solution prepared beforehand by dissolving 5.7 g of 30% aqueous hydrogen peroxide solution in 100 ml of glacial acetic acid was added dropwise to the chloroform solution at room temperature over a period of 30 minutes. This mixture was further stirred at room temperature for 24 hours. To the reaction mixture obtained was added 150 ml of water. This mixture was extracted with chloroform (50 ml×3), and the chloroform layer was washed with water and dried over anhydrous magnesium sulfate. Thereafter, the solvent was distilled off, and the white powder obtained in an amount of 522 mg was sufficiently washed with methanol. Thus, 485 mg of a reaction product (II) was obtained.

This reaction product (II) is the cyclic phenol sulfinyl compound represented by formula (1) wherein X=H, Y=t-Bu, n=4, and Z is sulfinyl.

Properties thereof are shown below.

Melting point: 210° C. (decomposition point)

$^1$H-NMR: (δ, ppm, Cl$_2$CDCDCl$_2$) 9.20 (s, 4H, OH), 7.61 (s, 8H, ArH), 1.26 (s, 36H, C(CH$_3$)$_3$)

$^{13}$C-NMR: (δ, ppm, Cl$_2$CDCDCl$_2$) 152.7, 142.4, 130.2, 128.0, 124.2, 122.8 (Ar) , 34.8 (C(CH$_3$)$_3$) , 31.4 (C(CH$_3$)$_3$)

FT-IR: (cm$^{-1}$, KBr): 3074 (br, OH), 2960 (s, CH$_3$), 1051, 998 (s, SO)

MS (m/z): 785 (M$^+$+1)

Elemental analysis %:

Calculated for C$_{40}$H$_{48}$S$_4$O$_8$: C, 61.20; H, 6.16; S, 16.34,

Found: C, 61.1; H, 6.3; S, 15.9.

EXAMPLE 2

Synthesis of 5,11,17,23-tetra-tert-butyl-25,26,27,28-tetrahydroxy-2,8,14,20-tetrasulfonyl-[19.3.1.1$^{3,7}$1$^{9,13}$1$^{15,19}$]octacosa-1(25),3,5,7(28),9,11,13(27),15,17,19(26),21,23-dodecaene (III)

In 30 ml of chloroform was dissolved 1.8 g of 5,11,17,23-tetra-tert-butyl-25,26,27,28-tetrahydroxy-2,8,14,20-tetrathia[19.3.1.1$^{3,7}$1$^{9,13}$1$^{15,19}$]-octacosa-1(25),3,5,7(28),9,11,13(27),15,17,19(26),21,23-dodecaene (I), represented by formula (2) wherein X=H, Y=t-Bu, and n=4. A solution prepared beforehand by dissolving 22.8 g of 30% aqueous hydrogen peroxide solution in 100 ml of glacial acetic acid was added dropwise to the chloroform solution at room temperature over a period of 30 minutes. This mixture was further stirred at room temperature for 48 hours. To the reaction mixture obtained was added 150 ml of water. This mixture was extracted with chloroform (50 ml×3), and the organic layer was washed with water and then dried over anhydrous magnesium sulfate. Thereafter, the chloroform was distilled off to obtain 740 mg of a white powder. This powder was sufficiently washed with methanol. Thus, 536 mg of a reaction product (III) was obtained.

This reaction product (III) is the cyclic phenol sulfonyl compound represented by formula (1) wherein X=H, Y=t-Bu, n=4, and Z is sulfonyl.

Properties thereof are shown below.

Melting point: 399° C. (decomposition point)

$^1$H-NMR: (δ, ppm, Cl$_2$CDCDCl$_2$) 8.05 (s, 8H, ArH), 1.28 (s, 36H, C(CH$_3$)$_3$)

$^{13}$C-NMR: (δ, ppm, Cl$_2$CDCDCl$_2$) 155.8, 143.3, 133.6, 128.9 (Ar), 34.9 (C(CH$_3$)$_3$), 31.2 (C(CH$_3$)$_3$ FT-IR: (cm$^{-1}$, KBr): ν 3409 (br, OH), 2996 (s, CH$_3$), 1308, 1164 (s, SO$_2$)

MS (m/z): 849 (M$^+$+1)

Elemental analysis %:

Calculated for C$_{40}$H$_{48}$S$_4$O$_{12}$: C, 56.58; H, 5.70; S, 15.11,

Found: C, 56.3; H, 5.7; S, 14.6.

EXAMPLE 3

Synthesis of 5,11,17,23-tetra-tert-butyl-25,26,27,28-tetrahydroxy-2,8,14,20-tetrasulfinyl-[19.3.1.1$^{3,7}$1$^{9,13}$1$^{15,19}$]octacosa-1(25),3,5,7(28),9,11,13(27),15,17,19(26),21,23-dodecaene (II)

In 65 ml of chloroform was dissolved 4 g of 5,11,17,23-tetra-tert-butyl-25,26,27,28-tetrahydroxy-2,8,14,20-tetrathia[19.3.1.1$^{3,7}$1$^{9,13}$1$^{15,19}$]octacosa-1(25),3,5,7(28),9,11,13(27),15,17,19(26),21,23-dodecaene (I), represented by formula (2) wherein X=H, Y=t-Bu, and n=4. To this chloroform solution was added 50 ml of glacial acetic acid to form a suspension. Thereto was added 2.44 g of sodium perborate monohydrate. This mixture was vigorously stirred at 50° C. for 4 hours, and 200 ml of water was added to the reaction mixture obtained. The resultant mixture was extracted with chloroform (50 ml×4) , and the chloroform layer was sufficiently washed with water and dried over anhydrous magnesium sulfate. Thereafter, the solvent was distilled off, and the white powder obtained in an amount of 3.39 g was recrystallized from chloroform/methanol to obtain 1.3 g of a crude reaction product (II). After the mother liquor was concentrated, recrystallization from chloroform/methanol was conducted. Thus, 0.92 g of a reaction product (II) was obtained.

This reaction product (II) is the cyclic phenol sulfinyl compound represented by formula (1) wherein X=H, Y=t-Bu, n=4, and Z is sulfinyl.

EXAMPLE 4

Synthesis of 5,11,17,23-tetra-tert-butyl-25,26,27,28-tetramethoxy-2-sulfinyl-8,14,20-trithia-[19.3.1.1$^{3,7}$1$^{9,13}$1$^{15,19}$]octacosa-1(25),3,5,7(28),9,11,13(27),15,17,19(26),21,23-dodecaene (IV)

In 20 ml of dichloromethane was dissolved 1.00 g of 5,11,17,23-tetra-tert-butyl-25,26,27,28-tetramethoxy-2,8,14,20-tetrathia[19.3.1.1$^{3,7}$1$^{9,13}$1$^{15,19}$]octacosa-1(25),3,5,7(28),9,11,13(27),15,17,19(26),21,23-dodecaene (V), represented by formula (2) wherein X=CH$_3$, Y=t-Bu, and n=4. To this dichloromethane solution was added 20 ml of a 10% potassium hydrogen carbonate solution. This mixture was vigorously stirred. The resultant suspension was cooled in a water bath, and 0.03 ml of bromine was gradually added thereto dropwise. The suspension was further stirred for 3 hours in a water bath. The reaction mixture obtained was separated into an aqueous layer and an organic layer. The aqueous layer was extracted with dichloromethane (20 ml×2), and the resultant dichloromethane solution was added to the organic layer obtained above. This mixture was sufficiently washed with saturated aqueous common-salt solution and then dried over anhydrous magnesium sulfate. Thereafter, the solvent was distilled off to obtain 1.02 g of a cream-colored powder. This powder was treated with silica gel column chromatography (dichloromethane) to separate 244 mg of a reaction product (IV) and by-products from the starting materials remaining unreacted.

This reaction product (IV) is the cyclic phenol sulfinyl compound represented by formula (1) wherein X=CH$_3$, Y=t-Bu, n=4, and one of the four Z's is sulfinyl.

Properties thereof are shown below.

Melting point: 291–292° C. (decomposition point)

$^1$H-NMR: (δ, ppm, Cl$_2$CDCDCl$_2$) 7.64, 7.57, 7.44 (m, 8H, ArH), 3.79, 3.48 (m, 12H, OCH$_3$), 1.24 (s, 36H, C(CH$_3$)$_3$) $^{13}$C-NMR: (δ, ppm, Cl$_2$CDCDCl$_2$) 158.62, 155.34, 146.99, 145.96, 144.11, 138.26, 135.17, 131.89, 128.88, 123.22 (Ar), 61.29, 59.42 (OCH$_3$), 34.33, 34.15 (C(CH$_3$)$_3$), 31.22 (C(CH$_3$)$_3$)

FT-IR: (cm$^{-1}$, KBr): ν 2961, 2866 (s, CH$_3$), 1051, 1002 (s, SO)

MS (m/z): 793 (M$^+$)

Elemental analysis %:

Calculated for C$_{44}$H$_{56}$O$_5$S$_4$: C, 66.63; H, 7.12,

Found: C, 66.5; H, 7.3

EXAMPLE 5

Synthesis of 5,11,17,23-tetra-tert-butyl-25,26,27,28-tetrahydroxy-2,8,14,20-tetrasulfonyl-[19.3.1.1$^{3,7}$1$^{9,13}$1$^{15,19}$]octacosa-1(25),3,5,7(28),9,11,13(27),15,17,19(26),21,23-dodecaene (III)

In 30 ml of chloroform was dissolved 1.8 g of 5,11,17,23-tetra-tert-butyl-25,26,27,28-tetrahydroxy-2,8,14,20-tetrathia[19.3.1.1$^{3,7}$1$^{9,13}$1$^{15,19}$]octacosa-1(25),3,5,7(28),9,11,13(27),15,17,19(26),21,23-dodecaene (I), represented by formula (3) wherein X=H Y=t-Bu and n=4. To this chloroform solution was added 25 ml of glacial acetic acid to form a suspension. Thereto was added 2.57 g of sodium perborate monohydrate. This mixture was vigorously stirred at room temperature for 5 days, and 100 ml of water was added to the reaction mixture obtained. The resultant mixture was extracted with chloroform (40 ml×2), and the chloroform layer was sufficiently washed with water and dried over anhydrous magnesium sulfate. Thereafter, the solvent was distilled off, and the white powder obtained in an amount of 1.45 g was sufficiently washed with methanol. Thus, 1.12 g of a reaction product (III) was obtained.

This reaction product (III) is the cyclic phenol sulfonyl compound represented by formula (1) wherein X=H, Y=t-Bu, n=4, and Z is sulfonyl.

APPLICATION EXAMPLE

The 5,11,17,23-tetra-tert-butyl-25,26,27,28-tetrahydroxy-2,8,14,20-tetrasulfinyl-[19.3.1.1$^{3,7}$1$^{9,13}$1$^{15,19}$]octacosa-1(25),3,5,7(28),9,11,13(27),15,17,19(26),21,23-dodecaene (II) produced in Example 1 and the 5,11,17,23-tetra-tert-butyl-25,26,27,28-tetrahydroxy-2,8,14,20-tetrasulfonyl-[19 3.1.1$^{3,7}$1$^{9,13}$1$^{15,19}$]octacosa-1(25),3,5,7(28),9,11,13(27),15,17,19(26),21,23-dodecaene (III) produced Example 2 were dissolved in an organic solvent, and these solutions were brought into contact with an aqueous solution containing sodium ions to conduct sodium ion extraction.

In 40 ml of chloroform were dissolved 16.0 mg of cyclic phenol sulfide (II) and 17.2 mg of cyclic phenol sulfide (III), respectively. These solutions were separately placed into a 200-ml separatory funnel together with 40 ml of an aqueous solution containing 20 ppm sodium ions. Each funnel was shaken for 5 hours. For the purpose of comparison, a mixture of 40 ml of chloroform containing neither cyclic phenol sulfide (II) nor (III) and 40 ml of an aqueous solution containing 20 ppm sodium ions was shaken for 5 hours in the same manner. After each sample was allowed to stand, the ion concentration in the aqueous solution was determined by the ICP-AES method (inductively coupled plasma-atomic emission spectrometry).

As a result, the sodium ion concentration in the aqueous solution of the sample containing cyclic phenol sulfide (II) after the extraction was found to be lower by 38% than that in the aqueous solution of the sample not containing cyclic phenol sulfide (II) after the test. Furthermore, the sodium ion concentration in the aqueous solution of the sample containing cyclic phenol sulfide (III) after the test was found to be lower by 58% than that in the aqueous solution of the sample not containing cyclic phenol sulfide (III) after the extraction.

It was thus found that by contacting the aqueous phase containing sodium ions with the organic phase containing either of the cyclic phenol sulfides synthesized in Examples 1 and 2, sodium ions can be extracted and transferred to the organic phase.

INDUSTRIAL APPLICABILITY

The cyclic phenol sulfide of the present invention is an entirely novel compound comprising phenol frameworks linked to each other with sulfide, sulfoxide, or sulfone bonds. It is useful, for example, as an antioxidant, a catalyst, a metal-trapping agent, a light sensor, an ion sensor, a sensor with substrate specificity, a separating-membrane material, a polymer material, a phase-transfer catalyst, an artificial enzyme, a light energy converter, or as an intermediate for functional molecules using a recognition ability of an ion or molecule.

We claim:

1. A cyclic phenol sulfide containing at least one sulfinyl or sulfonyl group represented by formula (1):

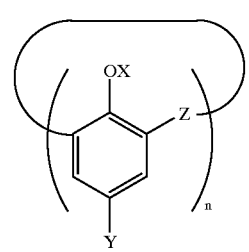

(1)

wherein X represents a hydrogen atom, a hydrocarbon group, or an acyl group; Y represents a hydrogen atom, a hydrocarbon group, a halogenated hydrocarbon group, —COR$^1$, —OR$^2$, —COOR$^3$, —CN, —CONH$_2$, —NO$_2$, —NR$^4$R$^5$, a halogen atom, —SO$_4$R$^6$, or —SO$_3$R$^7$, in which R$^1$, R$^2$, R$^3$, R$^4$, R$^5$, R$^6$, and R$^7$ each represents a hydrogen atom or a hydrocarbon group; Z represents one member selected from the group consisting of S, a sulfinyl group, and a sulfonyl group; and n represents an integer of 4 to 12, provided that the plural X's or the plural Y's are the same or different, and that at least one of the plural Z's is a sulfinyl group or a sulfonyl group.

2. A process for producing the cyclic phenol sulfide containing at least one sulfinyl or sulfonyl group represented by formula (1) as defined in claim 1, which comprises oxidizing a sulfide bond of a cyclic phenol sulfide represented by formula (2):

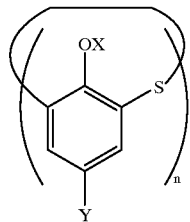

(2)

wherein X represents a hydrogen atom, a hydrocarbon group, or an acyl group; Y represents a hydrogen atom, a hydrocarbon group, a halogenated hydrocarbon group, —$COR^1$, —$OR^2$, —$COOR^3$, —CN, —$CONH_2$, —$NO_2$, —$NR^4R^5$, a halogen atom, —$SO_4R^6$, or —$SO_3R^7$, in which $R^1$, $R^2$, $R^3$, $R^4$, $R^5$, $R^6$, and $R^7$ each represents a hydrogen atom or a hydrocarbon group; and n represents an integer of 4 to 12, provided that the plural X's or the plural Y's are the same or different, with an oxidizing agent.

3. The process for producing a cyclic phenol sulfide according to claim 2, wherein the oxidizing agent is hydrogen peroxide, an organic peroxide, a peracid, a halogen oxide, an N-halogenated compound, a molecular halogen, oxygen, ozone, nitric acid, or an inorganic oxide.

4. The process for producing a cyclic phenol sulfide according to claim 2, wherein the oxidizing agent is hydrogen peroxide, a molecular halogen, or an inorganic oxide.

5. The process for producing a cyclic phenol sulfide according to claim 3, wherein the molecular halogen as the oxidizing agent is bromine.

6. The process for producing a cyclic phenol sulfide according to claim 3, wherein the inorganic oxide as the oxidizing agent is sodium perborate.

* * * * *